United States Patent [19]
Ueno

[11] Patent Number: 5,777,340
[45] Date of Patent: Jul. 7, 1998

[54] OPHTHALMIC PHOTOGRAPHIC DEVICE

[75] Inventor: Yasunori Ueno, Kanagawa-ken, Japan

[73] Assignee: Nikon Corporation, Tokyo, Japan

[21] Appl. No.: 877,726

[22] Filed: Jun. 18, 1997

Related U.S. Application Data

[63] Continuation of Ser. No. 445,101, May 19, 1995, abandoned.

[30]    Foreign Application Priority Data

May 20, 1994  [JP]  Japan .................................... 6-131174

[51] Int. Cl.$^6$ ................................ A61B 3/14; G03B 3/00
[52] U.S. Cl. ........................ 250/458.1; 351/206
[58] Field of Search ............................ 250/458.1, 459.1; 351/206

[56]         References Cited

U.S. PATENT DOCUMENTS

| | | | |
|---|---|---|---|
| 4,412,728 | 11/1983 | Sakane et al. | 351/206 |
| 4,436,388 | 3/1984 | Takahashi et al. | 351/206 |
| 5,181,055 | 1/1993 | Sano et al. | 351/206 X |
| 5,291,231 | 3/1994 | Hideshima et al. | 351/206 X |

FOREIGN PATENT DOCUMENTS 61-122837   6/1986   Japan .
62-41637    2/1987   Japan .

*Primary Examiner*—Edward J. Glick
*Attorney, Agent, or Firm*—Armstrong, Westerman, Hattori, McLeland & Naughton

[57]            ABSTRACT

An ophthalmic photographic device includes an illumination optical system for irradiating a fundus oculi of an eye to be examined with illuminating light, a photographic optical system to photograph fundus oculi, an indicator projecting optical system for projecting an indicator on the fundus oculi, and a focusing detection optical system which has a photoelectric converter receiving light of the indicator projected on the fundus oculi and detects focus information based on an output from the photoelectric converter. According to the present invention, the ophthalmic photographic device further includes a barrier filter for fluorescent photography which is used in fluorescent photography to cut off exciting light and to transmit fluorescent light from the fundus oculi and light having longer wavelengths than the fluorescent light over a predetermined wavelength range, and a barrier filter for infrared fluorescent photography which is used in infrared fluorescent photography to cut off exciting light and to transmit infrared fluorescent light from the fundus oculi and light having longer wavelengths than the infrared fluorescent light over a predetermined wavelength range. The barrier filters are adapted to be selectively used according to photographic conditions.

7 Claims, 3 Drawing Sheets

OPHTHALMIC PHOTOGRAPHIC DEVICE

This application is a continuation of application Ser. No. 08/445,101 filed May 19, 1995, now abandoned.

BACKGROUND OF THE INVENTION

1. Field of the Invention

The present invention relates to an ophthalmic photographic device, and more specifically to a retinal camera capable of detecting focusing in fluorescent fundus oculi photography and in infrared fluorescent fundus oculi photography as well as in ordinary photography.

2. Description of the Prior Arts

Conventional ophthalmic photographic devices like a retinal camera are known which can practice not only ordinary photography but also so-called fluorescent photography. In ordinary photography, an image of a fundus oculi to be examined is taken on color film, while in fluorescent photography, light having wavelengths in a specific visible wavelength range is projected on the fundus oculi to be examined and an image of blood vessels of the fundus oculi is taken by means of fluorescent light emitted from the blood vessels of the fundus oculi, which fluorescent light is exhibited by a fluorescent substance injected into an examinee.

As described above, in conventional ophthalmic photographic devices like a retinal camera, visible light is projected on the fundus oculi to be examined in ordinary and fluorescent photography. This has given rise to a problem that the state of a choroid located behind a retina cannot be observed or photographed with respect to a macula portion containing tissue which is opaque to visible light.

Thus, in order to detect in a patient senile macular degeneration or the like in its early stages, it has been practiced that infrared light having wavelengths in a specific wavelength range is projected on the fundus oculi to be examined to thereby observe and photograph the state of the choroid located behind the retina by means of infrared fluorescent light from the choroid coat.

Generally, it is difficult to focus on the fundus oculi for devices for observing or measuring an eye due to an insufficient quantity of light or poor contrast derived from a low reflectance of the fundus oculi. Particularly, observing an image of a fundus oculi by means of fluorescent light or infrared fluorescent light has involved a problem that it is more difficult for equipment (photographic optical system and observational optical system) to focus on a fundus oculi because an image of the fundus oculi to be observed has no coloration (if an observation system is a TV monitor, a monochromatic image will be displayed thereon) with resulting poor contrast.

SUMMARY OF THE INVENTION

A main object of the present invention is to provide an ophthalmic photographic device capable of detecting focusing in fluorescent photography and in infrared fluorescent photography as well as in ordinary photography.

Another object of the present invention is to provide an ophthalmic photographic device capable of detecting focusing in any of ordinary photography, fluorescent photography, and infrared fluorescent photography by selectively using a barrier filter for fluorescent photography and a barrier filter for infrared fluorescent photography.

A further object of the present invention is to provide an ophthalmic photographic device capable of detecting focusing in any of ordinary photography, fluorescent photography, and infrared fluorescent photography by selectively using an exciter filter for fluorescent photography and an exciter filter for infrared fluorescent photography in combination with the barrier filter for fluorescent photography and the barrier filter for infrared fluorescent photography.

The ophthalmic photographic device according to the present invention has an illumination optical system for irradiating a fundus oculi to be examined with illuminating light; a photographic optical system for photographing the fundus oculi; an indicator projecting optical system for projecting an indicator on the fundus oculi; a focusing detection optical system which has a photoelectric converter receiving light of the indicator projected on the fundus oculi and detects focusing information based on an output from said photoelectric converter; a barrier filter for fluorescent photography which cuts off exciting light in fluorescent photography and transmits, over a predetermined wavelength range, fluorescent light and light having a longer wavelength than fluorescent light, both of which are emitted from the fundus oculi; a barrier filter for infrared fluorescent photography which cuts off exciting light in infrared fluorescent photography and transmits, over a predetermined wavelength range, infrared fluorescent light and light having a longer wavelength than infrared fluorescent light, both of which are emitted from the fundus oculi. The barrier filters are adapted to be selectively used according to photographic conditions.

The barrier filter for fluorescent photography and the barrier filter for infrared fluorescent photography have a disadvantage in that extending their transmission characteristics to a shorter wavelength side allows even exciting light, together with fluorescent light and infrared fluorescent light, to pass therethrough. However, extending the transmission characteristic to the longer wavelength side does not bring about such a disadvantage. The present invention pays attention to this fact. The wavelength characteristic of the barrier filters is extended to the longer wavelength side so as not to transmit exciting light used in fluorescent photography and exciting light used in infrared fluorescent photography and to have no effect on photography. Thus, the ophthalmic photographic device is adapted for use in any of ordinary photography, fluorescent photography, and infrared fluorescent photography. That is, in ordinary photography, the barrier filters are not used at all, and in fluorescent photography, the barrier filter for fluorescent photography is used to prevent exciting light for fluorescent photography from advancing through the photographic optical system and to transmit light having useful wavelengths for fluorescent photography, thereby facilitating the focusing detection. Also, in infrared fluorescent photography, the barrier filter for infrared fluorescent photography is used to prevent exciting light from advancing through the photographic optical system and to transmit light having useful wavelengths for infrared fluorescent photography, thereby facilitating the focusing detection.

In an embodiment of the present invention, a luminescence center wavelength of the light source of the indicator projecting optical system is substantially longer than a center wavelength of infrared fluorescent light in infrared fluorescent photography, so that the barrier filters for fluorescent photography and for infrared fluorescent photography can transmit light emitted from the light source of the indicator projecting optical system. Also, the barrier filters for fluorescent photography and for infrared fluorescent photography may be selectively placed in a common optical path of the photographic optical system and the focus detecting optical system.

In another embodiment, an exciter filter which transmits light having an absorption center wavelength in fluorescent photography and an exciter filter which transmits light having an absorption center wavelength in infrared fluorescent photography may be provided, and the exciter filters may be selectively placed in the optical path of the illuminating optical system. Also, the exciter filters may be selectively disposed in the optical path between a stroboscopic tube and a wavelength separating member (a dichroic prism, in the embodiment of this application) in the illuminating optical system.

DESCRIPTION OF THE PREFERRED EMBODIMENT

An embodiment of the present invention will now be described with reference to the drawings.

Figure 1:
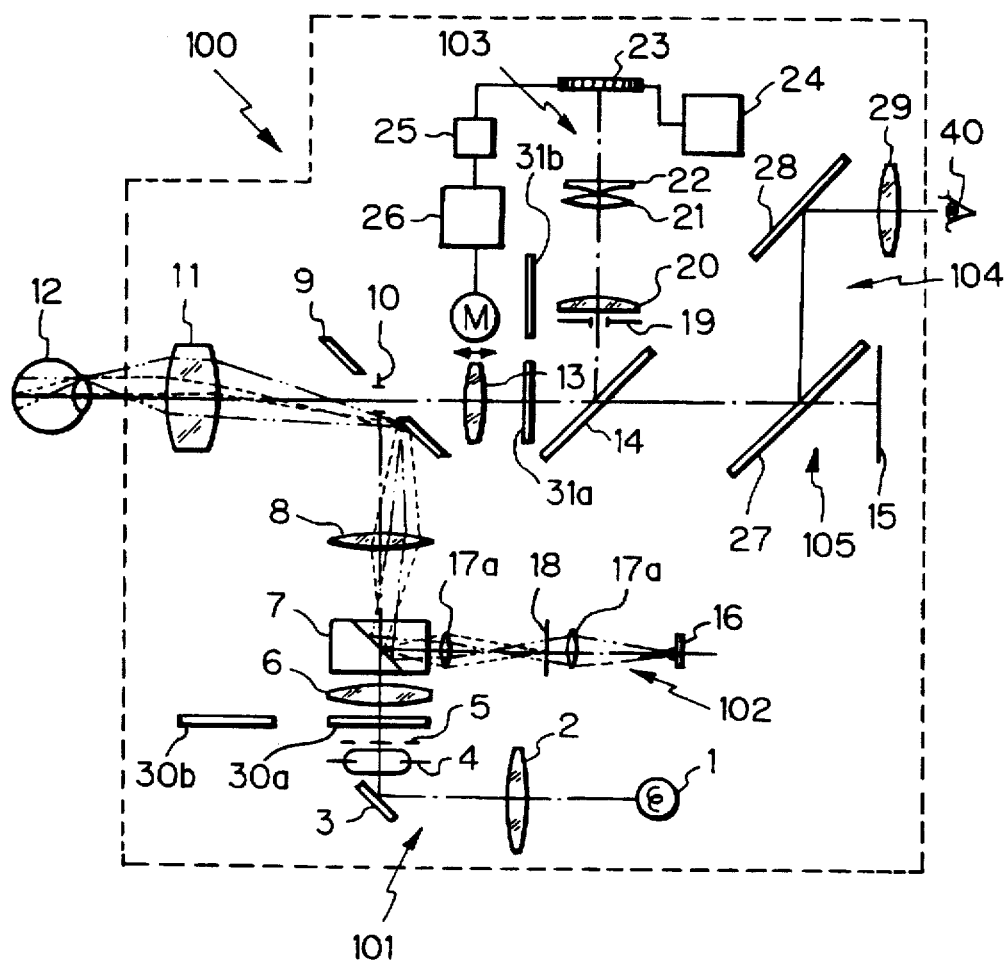
FIG. 1 is a schematic diagram wing the construction of an ophthalmic photographic device according to an embodiment of the present invention.

FIG. 1 is a schematic diagram showing the construction of an ophthalmic photographic device according to an embodiment of the present invention. An ophthalmic photographic device 100 comprises an illumination optical system 101 for illuminating a fundus oculi to be examined or tested, an indicator or collimating mark projecting optical system 102 for projecting an indicator or collimating mark on the fundus oculi, a focusing detection optical system 103 for receiving light of the indicator projected on the fundus oculi thereby to detect focusing on the fundus oculi, an observational optical system 104 for observing the state of the fundus oculi, and a photographic optical system 105 for photographing the state of the fundus oculi.

In FIG. 1, the illuminating optical system 101 includes a ring slit 5, a relay lens 6, a relay lens 2 for a light source 1, and a reflecting mirror 3. Light emitted from a light source 1 for observational illumination impinges on the reflecting mirror 3 through the relay lens 2 for a light source, and then is reflected upward in the figure. Light reflected by the reflecting mirror 3 impinges on the relay lens 6 through the ring slit 5.

Figure 3:
FIG. 3 is a view showing an opening of a ring slit.

A stroboscopic tube 4 is disposed as a light source for photographic illumination in a position where it is conjugated with the light source 1 for observational illumination by the relay lens 2 for a light source. Furthermore, as shown in FIG. 3, the ring slit 5 has an opening of a circular slit with an optical axis as a center thereof. An exciter filter 30a for fluorescent photography and an exciter filter 30b for infrared fluorescent photography are adapted to be selectively inserted between the ring slit 5 and the relay lens 6 for a ring slit.

The illumination optical system 101 further includes a wavelength separating member (a dichroic prism, in this embodiment) 7, a relay lens 8, an apertured mirror 9, and an objective lens 11, which components are all shared by the collimating mark or indicator projecting optical system 102. Light having passed through the relay lens 6 for a ring slit (light from the light source 1 for observational illumination and light from the stroboscopic tube 4) passes through the dichroic prism 7 and then impinges on the apertured mirror 9 through another relay lens 8 for a ring slit. Light reflected leftward in the figure by the apertured mirror 9 illuminates the fundus oculi of an eye 12 to be examined through the objective lens 11. As is well known, an operating distance between the device of the present embodiment and the eye 12 to be examined is adjusted so that the ring slit 5 is positioned so as to be substantially conjugated with the cornea of the eye 12 to be examined by the two relay lenses 6 and 8 for a ring slit and the objective lens 11.

Figure 4:
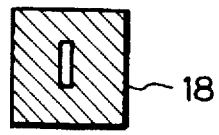
FIG. 4 is a view showing a slit formed in an indicator plate of FIG. 1.

On the other hand, the indicator projecting optical system 102 has a light source (point light source) 16 projecting an indicator or collimating mark and consisting of an infrared light emitting diode for example, a pair of relay lenses 17a and 17b, and an indicator plate 18 placed between the relay lenses 17a and 17b. Infrared light (indicated by a two dots-and-dash line in the figure) emitted from the light source 16 for projecting an indicator illuminates the indicator plate 18 through the relay lens 17a for the indicator projecting system. As shown in FIG. 4, a slit extending in parallel with the paper surface is formed in the indicator plate 18.

Beams of light having passed through the slit are once focused and then impinge on the dichroic prism 7 through the relay lens 17b for the indicator projecting system. Beams of light incident on the dichroic prism 7 are reflected upward by the reflecting surface thereof and then are refocused near the aperture mirror 9 through the relay lens 8 for a ring slit. Beams of light reflected leftward in the figure by the apertured mirror 9 are focused near the pupil of the eye 12 to be examined through the objective lens 11, thereby illuminating the fundus oculi.

In the above-mentioned illumination optical system 101 and indicator projecting optical system 102, the dichroic prism 7 has the characteristic of reflecting infrared light and of transmitting visible light. Accordingly, visible light from the light source 1 for observational illumination and from the stroboscopic tube 4 (light source for photographic illumination) passes through the dichroic prism 7 and advances toward the relay lens 8, while infrared light from the light source 1 for observational illumination and the stroboscopic tube 4 is reflected by the dichroic prism 7 to get out of the illuminating optical system. On the other hand, infrared light from the light source 16 for projecting an indicator is reflected by the dichroic prism 7 and then advances toward the relay lens 8.

As indicated by a dotted line in FIG. 1, rays of light having passed through the slit in the indicator plate 18 are focused near the dichroic prism 7 by the relay lens 17b for the indicator projecting system and then are reflected upward in the figure. The reflected beams of light are focused at a rear focal point of the objective lens 11 through the relay lens 8 and the apertured mirror 9. Thus, light having passed through the slit becomes substantially parallel beams of light after passing through the objective lens 11, and then enters the eye 12 to be examined. As a result, if the eye 12 to be examined is an emmetropia, an image of the slit in the indicator plate 18 is formed on the fundus oculi. In other words, an image of the slit in the indicator plate 18 (indicator image) defocuses according to the diopter of the eye 12 to be examined.

Figure 2:
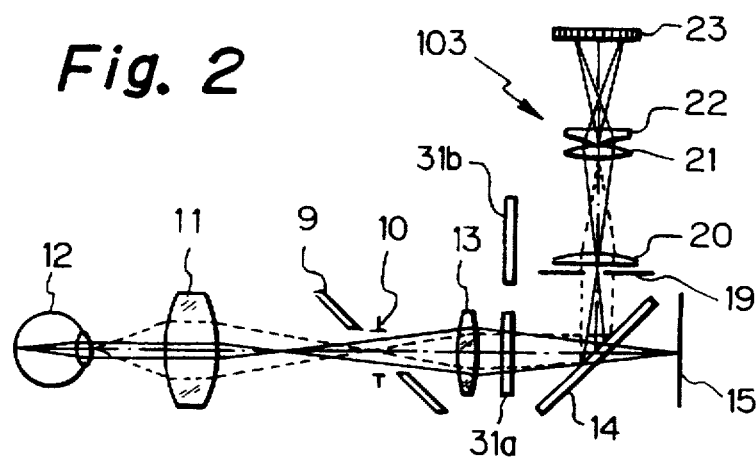
FIG. 2 is a partial diagrammatic view showing a focus detecting optical system of the ophthalmic photographic device of FIG. 1.

FIG. 2 is a partial diagrammatic view showing the structure of the focusing detecting optical system 103 of the ophthalmic photographic device of FIG. 1. The focusing detection optical system 103 includes a relay lens 13 for focusing, a wavelength separating member (a dichroic mirror, in this embodiment) 14, a field stop 19, a field lens 20 placed adjacent to the field stop 19, a refocusing lens 21, a pupil splitting prism 22 placed adjacent to the refocusing lens 21, and an array sensor 23. The observational optical system 104 and the photographic optical system 105, described later, share the relay lens 13 for focusing and the dichroic mirror 14. The field stop 19 is positioned so as to be conjugated with the array sensor 23 by the refocusing lens 21.

As indicated with a solid line in FIG. 2, an image of the slit in the indicator plate 18 projected on the fundus oculi of the eye 12 to be examined serves as a secondary light source. Beams of light from the secondary light source are once focused through the objective lens 11, pass through a center opening in the apertured mirror 9 and an aperture stop 10, and then enter the relay lens 13 for focusing. Infrared light having passed through the relay lens 13 for focusing impinges on the dichroic mirror 14 which has the characteristic of reflecting infrared light and of transmitting visible light. Beams of light reflected upward in the figure by the dichroic mirror 14 are once focused near the field stop 19 and then enter the field lens 20. Light having passed through the field lens 20 impinges on the array sensor 23 through the refocusing lens 21 and the pupil splitting prism 22.

In FIG. 1, the observational optical system 104 includes the relay lens 13 and dichroic mirror 14, which are shared by the focusing detection optical system 103, a quick return mirror 27, a mirror 28, and an eyepiece 29. The photographic optical system 105 has the shared relay lens 13 and dichroic mirror 14, and a photographic image plane 15. The array sensor 23 is positioned to be conjugated with the photographic image plane 15 and the image plane (not shown) of the eyepiece 29. A refocusing or image reforming lens, or TV image plane (both not shown) may be used in place of the eyepiece or an examiner or observer. This is preferable, in particular, the infrared fluorescent photography. Beams of reflected light from the fundus oculi of the eye 12 to be examined, which fundus oculi is illuminated by visible light from the light source 1 for observational illumination and the stroboscopic tube 4 (light source for photographic illumination), pass through the dichroic mirror 14 and then are focused on the photographic image plane 15. Since the quick return mirror 27 is located between the dichroic mirror 14 and the photographic image plane 15, the reflected visible light from the fundus oculi having passed through the dichroic mirror 14 is reflected upward in the figure by the quick return mirror 27 and then is led to the eyepiece 29 via the mirror 28 for observation by an examiner 40. The quick return mirror 27, mirror 28, eyepiece 29, and examiner 40 are not shown in FIG. 2.

Thus, the fundus oculi to be examined can be observed through the eyepiece 29 and photographed on the photographic image plane 15.

As has been described above, the dichroic prism 7 has the characteristic of reflecting infrared light and of transmitting visible light, and hence the fundus oculi of the eye 12 is illuminated by infrared light from the light source 16 for projecting an indicator or collimating mark and by visible light from the light source 1 for observational illumination and the stroboscopic tube 4.

Also, since the dichroic mirror 14 has the characteristic of reflecting infrared light and of transmitting visible light, only light which has passed through the indicator plate 18 illuminated with the light source 16 for projecting an indicator, reaches the array sensor 23. As a result, an indicator image (a slit image in the present embodiment) is formed with good contrast on the array sensor 23.

The barrier filter 31a for fluorescent photography and the barrier filter 31b for infrared fluorescent photography are adapted to be selectively inserted between the relay lens 13 for focusing and the dichroic mirror 14. This intends to pass only desired fluorescent light through the barrier filter in view of the fact that when fluorescent injected into blood vessels absorbs exciting light and emits fluorescent light, wavelength of fluorescent light shifts to the longer wavelength side than exciting light.

Thus, beams associated with the slit image (indicator image) from the fundus oculi of the eye 12 are focused near the array sensor 23 by the refocusing lens 21. At this time, the pupil splitting prism 22 causes a luminous flux to be split in half when the luminous flux passes therethrough. Each split luminous flux is focused on the array sensor 23 in mutually different areas (cells), as shown in FIG. 2.

Figure 5:
FIG. 5 is an external view of a pupil splitting prism of FIG. 1.

A perspective view of the pupil splitting prism 22 is shown in FIG. 5. In FIGS. 1 and 2, the ridge line of the pupil splitting prism 22 is perpendicular to the paper surface for convenience of representation. In actual disposition, however, the pupil splitting prism 22 is turned 90 degrees from the illustrated position about the optical axis so that the ridge line thereof is in parallel with the paper surface. As a result, cells of the array sensor 23 are arrayed perpendicular to the paper surface to be consistent with the direction of the ridge line of the pupil splitting prism 22. Thus, it is desirable for the longitudinal direction of the slit image and the direction of the ridge line of the pupil splitting prism 22 to match.

As indicated by a dotted line in FIG. 2, the ridge line of the pupil splitting prism 22 is substantially conjugated with the aperture diaphragm 10 by the relay lens 13 for focusing and the field lens 20. Since the aperture stop 10 is equivalent to an exit pupil of the focusing detection optical system 103, images on the array sensor 23 are formed by luminous flux from two different portions of the pupil of the optical system. Thus obtained two images on the array sensor 23, as is well known, shift laterally with respect to each other according to a so-called front focus state and rear focus state. Accordingly, by measuring the distance between the two images on the array sensor 23, the focusing state can be detected.

Figure 6:
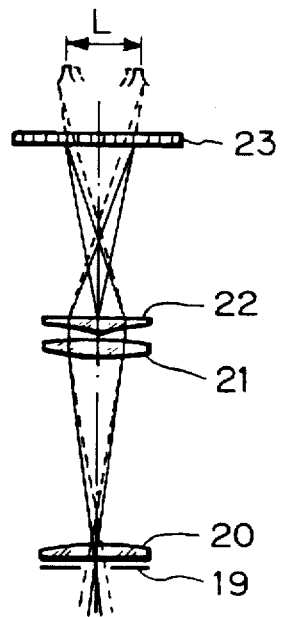
FIG. 6 is a diagram illustrating the principle of focusing detection.

In details, assuming that the distance between the two images on the array sensor 23 is L in the focused state, as indicated by a solid line in FIG. 6, when a focused point is located on the rear side of the field stop 19 (above the field stop 19 in the figure), such as in the rear focus state, the distance between images becomes smaller than the reference distance L, as indicated by a dotted line in the figure. On the other hand, when a focused point is located on the front side of the field stop 19 (below the field stop 19 in the figure), such as in the front focus state, the distance between images becomes larger than the reference distance L (not shown).

As has been described above, focusing information can be obtained by measuring the distance between two slit images on the array sensor 23 and by comparing the measured distance with a reference distance.

As shown in FIG. 1, cells of the array sensor 23 are sequentially driven based on signals from a drive means 24, and photoelectrically converted signals corresponding to the cells are sequentially outputted from the array sensor 23 to an arithmetic means 25. The arithmetic means 25 measures the distance between two slit images based on photoelectrically converted signals from the array sensor 23 and compares the measured distance with a reference distance measured in the focused state. Based on the focusing information thus obtained by the arithmetic means 25, a motor M is driven through a motor drive means 26 to move the relay lens 13 for focusing along the optical axis as needed thereby to focus the array sensor 23 on the fundus oculi of the eye 12 to be examined. This, in turn, focuses the photographic image plane 15 and the image plane (not shown) of the eyepiece 29 on the fundus oculi.

Incidentally, wavelengths required for ordinary fundus oculi photography range from about 350 nm to 750 nm, which wavelengths fall in the visible wavelength range. Also, in fluorescent photography, an absorption center wavelength is about 490 nm, while a fluorescence center wavelength is about 577 nm. In infrared fluorescent photography, an absorption center wavelength is about 766–795 nm, while a fluorescence center wavelength is about 826–835 nm.

Figure 7A:
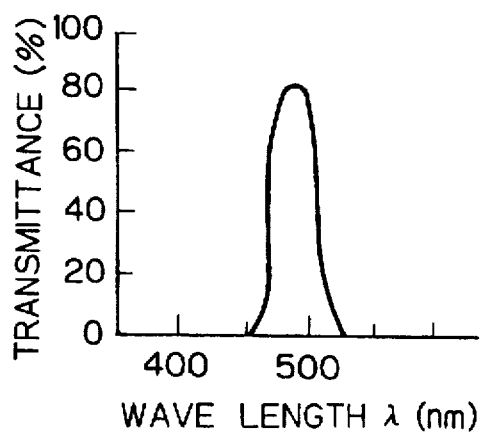
FIG. 7(a) is a graph showing a characteristic of an exciter filter used in fluorescent photography.
Figure 7B:
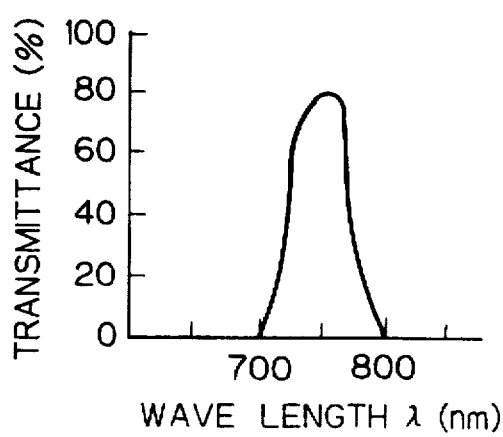
FIG. 7(b) is a graph showing a characteristic of an exciter filter used in infrared fluorescent photography.
Figure 8A:
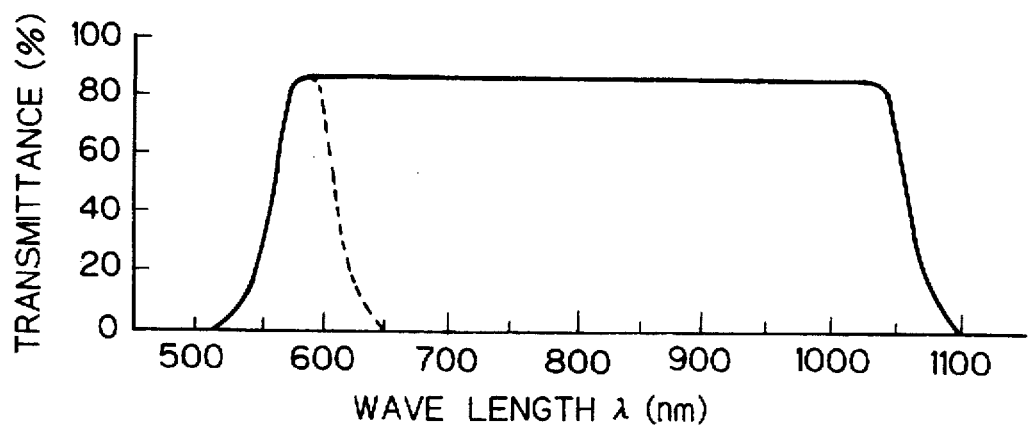
FIG. 8(a) is a graph showing a characteristic of a barrier filter used in fluorescent photography.
Figure 8B:
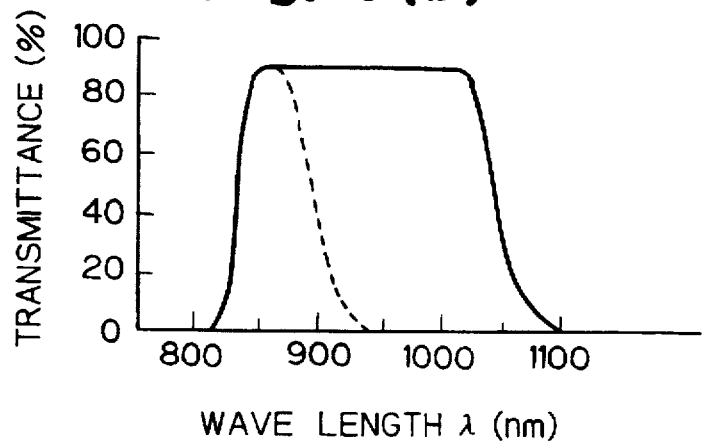
FIG. 8(b) is a graph showing a characteristic of a barrier filter used in infrared fluorescent photography.

Hence, in the present embodiment, a filter having a transmission characteristic as shown in FIG. 7(a) so as to transmit only exciting light corresponding to the above wavelength condition for fluorescent photography is used as the exciter filter 30a for fluorescent photography, and a filter having a transmission characteristic as shown in FIG. 7(b) so as to transmit only exciting light corresponding to the above wavelength condition for infrared fluorescent photography is used as the exciter filter 30b for infrared fluorescent photography. Also, a filter having a transmission characteristic shown in FIG. 8(a) is used as the barrier filter 31a for fluorescent photography, and a filter having a transmission characteristic shown in FIG. 8(b) is used as the barrier filter 31b for infrared fluorescent photography.

As seen from FIG. 8, the transmission characteristic of the barrier filters 31a and 31b is extended only to the longer wavelength side. Thus, the barrier filter 31a does not transmit exciting light (about 450–525 nm) which has passed through the exciter filter 30a having a transmission characteristic shown in FIG. 7(a), but can transmit fluorescent (about 520–650 nm) in fluorescent photography and light having longer wavelengths than the fluorescent light. Also, the barrier filter 31b does not transmit exciting light (about 700–800 nm) which has passed through the exciter filter 30b having a transmission characteristic shown in FIG. 7(b), but can transmit infrared fluorescent light (about 820–940 nm) in infrared fluorescent photography and light having longer wavelengths than the infrared fluorescent light.

These characteristics reveal that in order to detect focusing in any of ordinary photography, fluorescent photography, and infrared fluorescent photography, at least, a center wavelength of the light source 16 for projecting an indicator or collimating mark should be substantially longer than a center wavelength of infrared fluorescent light. At this time, light from the light source 16 needs to pass through both the barrier filter for fluorescent photography and the barrier filter for infrared fluorescent photography. Furthermore, the dichroic mirror 14 has the characteristic of reflecting light of the light source 16, which light has substantially longer wavelengths than a center wavelength of infrared fluorescent light, and of transmitting light having shorter wavelengths than a center wavelength of infrared fluorescent light. The dichroic prism 7 has, also, a characteristic of reflecting light from the light source 16 and transmitting light having wavelength shorter than that of light form the light source 16. A dichroic mirror may be used in place of the dichroic prism.

Photographic methods using the above-mentioned ophthalmic photographic device according to the present embodiment will now be described briefly.

Ordinary Photography

In this case, neither of the exciter filters is placed between the ring slit 5 and the relay lens 6, and neither of the barrier filters is placed between the relay lens 13 for focusing and the dichroic mirror 14. Accordingly, the fundus oculi of the eye 12 to be examined is illuminated by light from the light source 1 for observational illumination in the illuminating optical system 101 and by infrared light from the light source 16 for projecting an indicator in the indicator projecting optical system 102. An image of the fundus oculi is focused by the focusing detection optical system 103 in the manner described before by means of infrared light reflected by the dichroic mirror 14. The observational optical system 104 allows an examiner to observe the image of the fundus oculi. The image of the fundus oculi is photographed on the photographic image plane 15 by light emitted from the stroboscopic tube 4.

Fluorescent Photography

In this case, the exciter filter 30a is placed in the optical path between the ring slit 5 and the relay lens 6, and the barrier filter 31a is placed in the optical path between the relay lens 13 for focusing and the dichroic mirror 14. Accordingly, the fundus oculi to be examined is illuminated by exciting light, i.e., light which has passed through the exciter filter 30a after having been emitted from the light source 1 for observational illumination in the illuminating optical system 101, and by infrared light from the light source 16 for projecting an indicator in the indicator projecting optical system 102. The exciting light causes the fundus oculi to emit fluorescent light. Fluorescent light and infrared light reflected by the fundus oculi pass through the objective lens 11 and the relay lens 13 for focusing and then advance through the focusing detection optical system 103 and the observational optical system 104. An image of the fundus oculi is focused by the focusing detection optical system 103 in the manner described before by means of infrared light reflected by the dichroic mirror 14. The observational optical system 104 allows an examiner to observe the image of the fundus oculi having passed through the dichroic mirror 14. When the image of the fundus oculi is to be photographed, the quick return mirror 27 is lifted up, and the image is photographed on the photographic image plane 15 by fluorescent light which is emitted from the fundus oculi as a result of stimulation by excitation light, i.e. light which has passed through the exciter filter 30a after having been emitted from the stroboscopic tube 4.

Infrared Fluorescent Photography

In this case, the exciter filter 30b is placed in the optical path between the ring slit 5 and the relay lens 6, and the barrier filter 31b is placed in the optical path between the relay lens 13 for focusing and the dichroic mirror 14.

Accordingly, the fundus oculi to be examined is illuminated by exciting light, i.e., light which has passed through the exciter filter 30b after having been emitted from the light source 1 for observational illumination in the illuminating optical system 101, and by infrared light from the light source 16 for projecting an indicator in the indicator projecting optical system 102. Exciting light causes the fundus oculi to emit infrared fluorescent light. Infrared fluorescent light and infrared light reflected by the fundus oculi pass through the objective lens 11 and the relay lens 13 for focusing and then advance through the focusing detection optical system 103 and the observational optical system 104. An image of the fundus oculi is focused by the focusing detection optical system 103 in the manner described before by means of infrared light reflected by the dichroic mirror 14. The observational optical system 104 allows an examiner to observe the image of the fundus oculi by means of light having passed through the dichroic mirror 14 (in this case TV monitor is preferable). When the image of the fundus oculi is to be photographed, the quick return mirror 27 is lifted up, and the image is photographed on the photographic image plane 15 by infrared fluorescent light which is emitted from the fundus oculi as a result of stimulation by exciting light, i.e., light which has passed through the exciter filter 30b after having been emitted from the stroboscopic tube 4.

As has been described above, the ophthalmic photographic device of the present invention enables focus to be detected in fluorescent photography and infrared fluorescent photography as well as ordinary photography.

What is claimed is:

1. An ophthalmic photographic device comprising:

an illumination optical system for irradiating a fundus oculi to be examined with illuminating light said illumination system comprising a wavelength separating member;

a photographic optical system for photographing the fundus oculi;

an indicator projecting optical system for projecting an indicator on the fundus oculi via said wavelength separating member of said illumination optical system;

a focusing detection optical system which has a photoelectric converter receiving light of the indicator projected on the fundus oculi and detects focusing information based on an output from said photoelectric converter, said focusing detection optical system including a dichroic mirror which reflects light having substantially longer wavelengths than a center wavelength of infrared fluorescent light for use in detecting focusing information;

a barrier filter for fluorescent photography which cuts off exciting light in fluorescent photography and transmits, over a predetermined wavelength range, fluorescent light and light having a longer wavelength than fluorescent light, both of which are emitted from the fundus oculi;

a barrier filter for infrared fluorescent photography which cuts off exciting light in infrared fluorescent photography and transmits, over a predetermined wavelength range, infrared fluorescent light and light having a longer wavelength than infrared fluorescent light, both of which are emitted from the fundus oculi; and said barrier filters being adapted to be selectively used according to photographic conditions;

wherein a luminescence center wavelength of a light source of said indicator projecting optical system is substantially longer than a center wavelength of infrared fluorescent light in infrared fluorescent photography, so that said barrier filters for fluorescent photography and for infrared fluorescent photography transmit light emitted from the light source of said indicator projecting optical system.

2. An ophthalmic photographic device according to claim 1, wherein said barrier filters for fluorescent photography and for infrared fluorescent photography are adapted to be selectively placed in a common optical path of said photographic optical system and said focusing detecting optical system.

3. An ophthalmic photographic device according to claim 2, wherein said barrier filters for fluorescent photography and for infrared fluorescent photography are adapted to be selectively placed in the common optical path between an aperture stop and a wavelength separating member.

4. An ophthalmic photographic device according to claim 2, further comprising an exciter filter transmits light having an absorption center wavelength in fluorescent photography and an exciter filter transmits light having an absorption center wavelength in infrared fluorescent photography, which exciter filters are adapted to be selectively placed in an optical path of said illumination optical system.

5. An ophthalmic photographic device according to claim 4, wherein said exciter filters are adapted to be selectively placed in the optical path between a stroboscopic tube and said wavelength separating member in said illumination optical system.

6. An ophthalmic photographic device according to claim 1, further comprising an exciter filter transmits light having an absorption center wavelength in fluorescent photography and an exciter filter transmits light having an absorption center wavelength in infrared fluorescent photography, which exciter filters are adapted to be selectively placed in an optical path of said illumination optical system.

7. An ophthalmic photographic device according to claim 6, wherein said exciter filters are adapted to be selectively placed in the optical path between a stroboscopic tube and said wavelength separating member in said illumination optical system.

* * * * *